United States Patent [19]
Yabrov et al.

[11] Patent Number: 4,788,143
[45] Date of Patent: Nov. 29, 1988

[54] METHOD FOR DETERMINING LEVELS OF CELL-MEDIATED IMMUNITY

[76] Inventors: Alexander A. Yabrov, 70 Roper Rd., Princeton, N.J. 08540; Theodore Khavkin, 126 Montgomery St., Apt 2F, Highland Park, N.J. 08904

[21] Appl. No.: 605,321

[22] Filed: Apr. 30, 1984

[51] Int. Cl.$^4$ .............................................. C12Q 1/02
[52] U.S. Cl. .................................... 435/29; 435/2; 435/4; 435/19; 435/21; 435/172.2; 435/240.21; 435/240.25; 435/240.26; 935/93; 935/95; 935/110; 436/506; 436/800; 436/811; 436/827; 424/3
[58] Field of Search ................... 435/2, 4, 19, 21, 29, 435/172.2, 240, 241, 240.1, 240.26; 935/89, 93, 95, 110; 436/506, 800, 811, 827; 424/3

[56] References Cited

U.S. PATENT DOCUMENTS

4,343,895  8/1982  Sugaar ................................. 435/6

OTHER PUBLICATIONS

Sanderson, R. J. et al., Journal of Immunology, 118:1409–1414 (Apr. 1977).
Leak, L. V. et al., J. Ultrastructure Research 86(1):1–17 (1984) cited in Chemical Abstract CA101(9):70792n.
Abe, E. et al., Proc. Natl. Acad. Sci, U.S.A., 80:5583–5587 (9–1983).
Sone, S. et al., Amer. J. Pathology, 103(2):234–246 (May 1981) cited in Medline Abstract 81204603.
Chambers, T. J., J. Pathology 123(1):53–62 (1977) cited in Biosis Abstract 78:138329.
Stadler, B. M. et al., European J. Immunology 8:243–246 (1978).
Nathan, C. F. et al., J. Experimental Medicine 158:670–689 (9–1983).
Phondke, G. P. et al., J. Nat. Cancer Inst. 66:637–642 (1981) cited in Medline Abstract 81195335.
Postlethwaite, A. E. et al., J. Exp. Med. 155:168–178 (1–1982).
Dianzani, F. et al., *Human Lymphokines*, A. Khan et al., eds, Academic Press, N.Y. (1982), pp. 527–536
De Ley, M. et al., Ibid, pp. 257–263.
Bursuker et al., Journal of the Reticuloendothelial Society, vol. 33, pp. 207–220, 1983.
Coonrod et al., *The Journal of Immunology*, vol. 106, pp. 209–216, 1971.
Dean, Jack H., in *Immunodiagnosis of Cancer*, Herberman and McIntire (eds.), Marcel Dekker, Inc., New York, 1979, pp. 738–769.
D'Onofrio et al., *Immunobiol.*, vol. 164, pp. 13–22, 1983.
Schreiber et al., *Immunology*, Paper 363, pp. 231–238, 1983.
Todd et al., *Transactions of the Royal Society of Tropical Medicine and Hygiene*, vol. 75, pp. 783–787, 1981.

*Primary Examiner*—Margaret Moskowitz
*Attorney, Agent, or Firm*—Irene J. Frangos

[57] ABSTRACT

A patient's level of cell-mediated immunity is determined by obtaining a blood sample from the patient, incubating cells from the sample in a tissue culture medium containing Concanavalin A, and observing the number of polykaryons produced or the number of nuclei per polykaryon or both to thereby determine the level of cell-mediated immunity of the hose from which the blood sample was obtained.

12 Claims, 2 Drawing Sheets

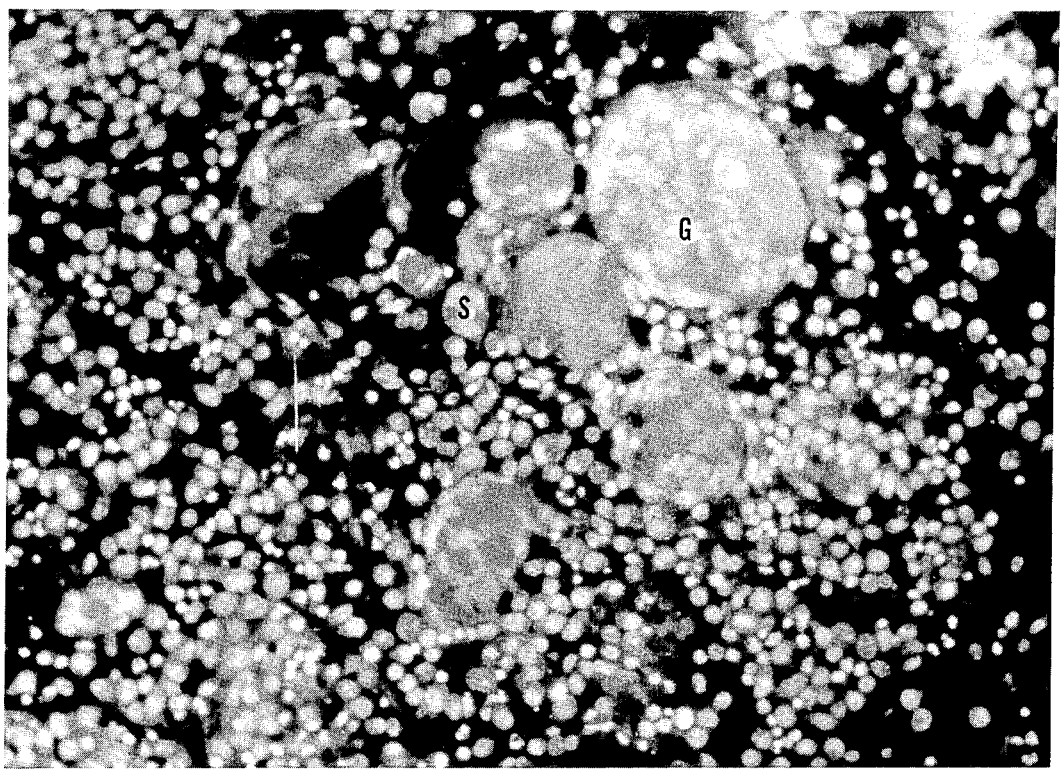
FIG. I
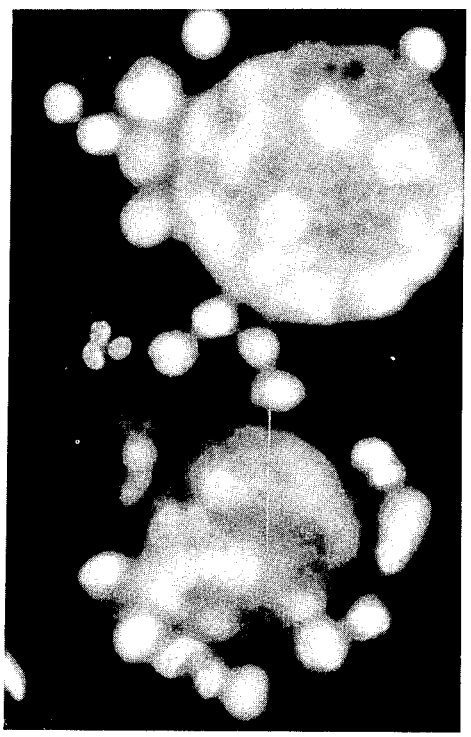
FIG. 2A
FIG. 2B

METHOD FOR DETERMINING LEVELS OF CELL-MEDIATED IMMUNITY

BACKGROUND OF THE INVERNTION

1. Field of the Invention

This invention relates to medical diagnosis and, in particular, to a technique for determining a patient's level of cell-mediated immunity.

2. Description of the Prior Art

As understood in the art, cell-mediated immunity is a form of nonspecific and/or acquired immunity involving various white blood cells, particularly, lymphocytes of thymic origin, i.e., T-lymphocytes, and monocytes. Immunity of this type is responsible for resistance to infectious diseases caused by certain bacteria, fungi and viruses, and plays a role in certain allergies. Cell-mediated immunity is also involved in certain aspects of an individual's resistance to cancer, in delayed hypersensitivity reactions, certain autoimmune diseases and in the rejection of allografts.

Lymphocytes and monocytes are the main effector cells involved in cell-mediated immunity. In response to various stimulants, these cells influence each other both by physical contacts and by the release of active substances, i.e., lymphokines and monokines. Changes in the mutual interactions of these cells generally result in changes in the level of cell-mediated immunity exhibited by the body in response to challenges.

The level of cell-mediated immunity expressed by patients varies with the character and stage of their disease. It is increased in allergic and autoimmune diseases, especially during their acute stages.

It is suppressed in cancer and some other diseases, as for instance in some systemic diseases (lupus erythematosus, multiple sclerosis), in the acute stage or in exacerbation of bacterial diseases such as tuberculosis and leprosy, in acute viral diseases, in bacterial intoxications, as well as in the course of immunosuppressive therapy using corticosteroids, antithymocyte immune globulin (ATG) or cyclosporin A. Also, some noninfective diseases, e.g., diabetes, as well as traumas and surgical operations, may be complicated by the suppression of cell-mediated immunity.

The suppression is often associated with an unfavorable outcome for the patient. Successful treatment of the patient's disease manifests itself by the normalization of the cell-mediated immune response of the body. Consequently, evaluation of cell-mediated immunity provides important information concerning the state of the patient and the efficacy of the treatment applied.

In addition to providing a method for evaluating the course of treatment of such diseases as cancer, the ability to determine an individual's level of cell-mediated immunity has numerous other important clinical and experimental applications. For example a method for evaluating the level of cell-mediated immunity can be used to study acquired and genetically determined immunodeficient states. It can also be used as a screening method to determine serum factors which suppress or alter the cell-mediated immunity response. Further, a method for determining the level of cell-mediated immunity can be used to study the mechanisms of lymphokine and monokine production and regulation. A discussion of these and other applications for methods for measuring cell-mediated immunity can be found in the recent review entitled *Immunodiagnosis of Cancer*, edited by Ronald B. Herberman and K. Robert McIntire, Marcel Dekker, Inc., New York, 1979. See in particular chapter 5.3, entitled "Application of the Microculture Lymphocyte Proliferation Assay to Clinical Studies," Jack H. Dean, Litton Bionetics, Inc., Kensington, Md., pages 738-769.

At present, a patient's level of cell-mediated immunity is determined through a battery of tests, usually applied concurrently. The level of cell-mediated immunity is determined by comparing and summarizing the results of the various tests. One such test which has been used to evaluate the level of cell-mediated immunity has involved the reaction of leukocytes to mitogens.

Mitogens are agents which stimulate cell division, i.e., mitosis. Among the mitogens used for immunological assays are mitogenic lectins extracted from plants, such as, Concanavalin A (Con A) and phytochemagglutinin. These agents are effective in inducing proliferation of T-lymphocytes.

Mitogens are used to determine a patient's level of cell-mediated immunity by measuring the extent of lymphocyte activation and proliferation induced in response to a mitogen. The intensity of DNA or protein synthesis by lymphocytes is used as a marker of lymphocyte activation in such assays. A radio-labeled precursor of DNA, e.g., thymidine, or of protein, e.g., leucine, is added to a suspension of mitogen-stimulated lymphocytes taken from the patient whose level of cell-mediated immunity is to be determined. Incorporation of the labeled material into the patient's lymphocytes is measured and compared with the level of incorporation by normal lymphocytes.

Use of this method gives information regarding the level of cell-mediated immunity based on the response of lymphocyte cells. Significantly, it does not provide information regarding the monocyte component of the cell-mediated immunity response.

The activity of monocytes and monocyte-derived macrophages is measured by their capacity to ingest particles (phagocytosis) and by their migration toward certain antigens (macrophage migration or chemotaxis). None of these tests for monocyte and monocyte-derived macrophages have used mitogens and, in particular, none of these tests have used mitogens for the evaluation of macrophage and monocyte behavior in the cell-mediated immunity response.

Monocytes and monocyte-derived macrophages are known to display the ability to fuse and to form polynuclear cells (hereinafter referred to as polykaryons) under various pathological and experimental conditions. Specifically, the polykaryons generally appear in inflammatory foci elicited by the same immunological stimuli, e.g., bacteria, fungi and viruses, which cause the establishment of cell-mediated immunity, as well as in cell cultures. Such an ability has never been used for evaluation of cell-mediated immunity.

In summary, to date, mitogens have been used to evaluate levels of cell-mediated immunity only by their influence on proliferation of lymphocytes. The proliferation has been assayed by means of the incorporation of radio-labeled precursors of DNA or protein into the lymphocytes undergoing proliferation.

SUMMARY OF THE INVENTION

It is an object of the present invention to provide a method for determining a patient's level of cell-mediated immunity. It is a further object of the invention to provide a method for determining a patient's level of cell-mediated immunity based on the monocyte contribution to the cell-mediated immunity response, as an alternative to the lymphocyte contribution. It is a further object of the invention to provide a method for measuring cell-mediated immunity using mitogens which is simpler and easier to use than prior methods using mitogens and which does not involve the use of radio-labeled materials. It is an additional object of the invention to provide a method for measuring cell-mediated immunity in which the response of monocytes to mitogens is assayed rather than the response of lymphocytes to mitogens.

In accordance with the invention, it has been found that the exposure of human leukocytes growing in suspension to the mitogen Concanavaline A, and only this mitogen, results in a prompt and mass formation of monocyte polykaryons. Moreover, the size and the number of polykaryons produced in response to treatment with Concanavalin A vary with the level of cell-mediated immunity of the host from which the leukocytes were obtained.

The yield of monocyte polykaryons depends on the conditions of the culture, in particular, on the cell concentration, and—other things being equal—on the level of cell-mediated immunity of the host. Concanavalin A has been found to induce polykaryon appearance in leukocyte cultures containing from $10^4$ to $10^8$ cells per ml. A cell concentration ranging from about $1 \times 10^6$ to about $3 \times 10^6$ cells/ml has been found particularly suitable for the assessment of cell-mediated immunity. Thus, for individuals having normal levels of cell-mediated immunity, a relatively large number of polykaryons, on the order of 30 to 100 polykaryons per approximately $10^6$ leukocytes, are produced. Also, for these individuals, a full spectrum of polykaryons is found including small polykaryons having between 2 and 9 nuclei, medium sized polykaryons having between 10 and 20 nuclei and giant polykaryons having more than 20 and sometimes hundreds of nuclei. On the other hand, for individuals having a decreased level of cell-mediated immunity, few polykaryons are found, e.g., on the order of 0 to 10 polykaryons per approximately $10^6$ leukocytes, and these polykaryons are typically small or medium polykaryons, as opposed to giant polykaryons.

The present invention is easily practiced in the following manner. First, a sample of blood is taken from the host whose level of cell-mediated immunity is to be determined. This sample is either fractionated to remove red blood cells or is diluted, and the resulting cell suspension is incubated in a tissue culture medium to which has been added a sufficient amount of Concanavalin A (Con A) to induce the polykaryon response. Typically, the polykaryons appear within the first day of stimulation with Con A. The formation and growth of the polykaryons lasts for about three days and then typically declines. This differs from the polykaryon formation in other previously known monocyte (macrophage) culture systems in which the cell fusion appears to be a time dependent event or both a time dependent and an adherence dependent event, and results in the formation of long-lived polykaryons whose appearance is not connected with direct action of the mitogen.

The level of cell response can be evaluated at any time during the tissue culture process, but is preferably evaluated between about 24 and about 48 hours after exposure of the cells to Con A. A quantitative analysis of the polykaryon response can be done by incubating the culture with a fluorescent vital stain and then observing samples taken from the culture under a fluorescent microscope. Also, polysaccharide, and in particular, glycogen, stains, e.g., a periodic acid-Schiff stain, can be used since it has been found that the polykaryons are rich in polysaccharides, in general, and glycogen, in particular. Other stains, such as, stains for nonspecific esterase and acid phosphatase, can also be used, and a precise quantitative analysis can be obtained through the use of a cytocentrifuge.

In comparison with the lymphocyte proliferation test used in the prior art, the present invention provides additional information not provided by the prior technique. Specifically, the present invention provides information regarding the contribution of monocytes to cell-mediated immunity. In particular, it provides information regarding the capacity of monocytes to respond to Concanavalin A so as to fuse and form polykaryons. In practice, the technique of the present invention and the lymphocyte proliferation test can be used together to provide an even more detailed evaluation of a patient's level of cell-mediated immunity.

BRIEF DESCRIPTION OF THE DRAWINGS

FIG. 1 is a fluorescent photomicrograph (acridine-orange stain) of living cells at a power of $10\times$ showing giant (G) and small (S) polykaryons produced by exposure of a leukocyte preparation from a normal individual to Concanavalin A (Con A).

FIG. 2 consists of two fluorescent photomicrographs (vital acridine-orange stain) at $40\times$ showing the same polykaryons produced under the same conditions as those of FIG. 1. FIG. 2a selectively shows green fluorescence of nuclei; FIG. 2b shows red fluorescence of numerous lysosomes.

DESCRIPTION OF THE PREFERRED EMBODIMENTS

Figure 3:
FIG. 3 is a photomicrograph (Giemsa stained cytospin smear) at $100\times$ showing a medium-sized polykaryon produced under the same conditions as in FIG. 1.

As discussed above, the present invention relates to a method for determining a patient's level of cell-mediated immunity. The method involves obtaining a blood sample from a host, incubating cells from the sample in a tissue culture medium including Con A, and observing the number of polykaryons produced or the number of nuclei per polykaryon or both to thereby determine the level of cell-mediated immunity of the host from which the blood sample was obtained.

A peripheral whole blood sample is obtained from the host in the standard way, and, for later quantification, the number of leukocytes per milliliter and the cell differential (percent granulocytes, lymphocytes and monocytes) is determined. Normally, the whole blood will be heparinized with preservative-free heparin (50 IU/ml).

The induction of polykaryons can be carried out either in the presence of erythrocytes or the sample of whole blood can be fractionated by, for example, a Ficoll-Hypaque gradient, to remove the erythrocytes and most of the granulocytes. As typical Ficoll-Hypaque separation procedure suitable for use with the present invention is as follows.

First, the sample of whole blood is diluted 1:2 with phosphate buffered saline. Ten milliliters of the diluted whole blood is added to 5 milliliters of Ficoll-Hypaque and the suspension is placed in a 15 milliliter centrifuge tube and centrifuged at 250×g for 30 minutes. Ficoll-Hypaque having a specific density of 1.077±0.001 has been found to give both good separation and good yield. It has also been found preferable to use room temperature Ficoll-Hypaque to optimize the cell separation.

After the cell and Ficoll-Hypaque suspension has been centrifuged, the leukocytes are removed from the gradient interface, care being taken to obtain both the pellet and the cells from the area immediately below the gradient interface since this sub-interface region typically includes numerous monocytes. The leukocytes thus obtained are washed twice for 10 minutes in phosphate buffered saline. During the first wash, care is taken to spin the cells at a sufficient speed, e.g., 250×g, to prevent establishing a secondary gradient with the residual Ficoll-Hypaque in the wash mixture. The second wash is normally performed at a lower speed, e.g., 120×g. The washed leukocytes are resuspended in a protein-containing tissue culture medium as described below.

If fractionation of the whole blood sample is not performed, the sample of whole blood is diluted 1:10 with tissue culture medium.

Various tissue culture media known in the art can be used with the present invention. Typically, an antibiotic, such as gentamicin at a dosage of 50 mg/ml, should be included in the medium. Also, for fractionated whole blood, it has been found that a carefully controlled amount of protein must be added to the medium. Excessive or limited protein has been found to result in the inhibition of polykaryon formation. A protein concentration ranging from about 1.00 mg/ml to about 6.00 mg/ml has been found suitable for polykaryon stimulation, with the preferred protein concentration being about 1.25 mg/ml. For the whole blood preparation, protein need not be added, there generally being sufficient protein for polykaryon formation in the whole blood sample.

A particularly suitable tissue culture medium for use in the present invention is a RPMI-1640 medium, such as that sold by Pharmacia of Piskataway, N.J., to which has been added 50 mg/ml of gentamicin. For fractionated whole blood, a particularly suitable source of protein is human aγ serum, having a protein content on the order of 25 mg/ml. Typically, sufficient serum is added to the medium to produce a final concentration of between about 2.5% and about 20%, the preferred concentration being about 5%.

The aγ serum for use in the medium can be prepared in the following way. First, human plasma is obtained from a suitable source, such as, the American Red Cross. Plasma from a number of donors, e.g., one hundred, is pooled and stirred for three hours at room temperature in a large beaker containing glass beads. A sufficient amount of calcium chloride is added to the plasma to produce a calcium chloride concentration of 0.02M±0.005M.

After the three hours of mixing, the plasma is stored for a minimum of 10 hours at 2° C. to 8° C. Thereafter, the clot which forms is removed and the plasma is centrifuged either at 4500×g for 45 minutes or at 18,000–22,000×g for 1.5 minutes at a temperature of between 2° C. and 8° C. To the supernatant (serum) is then added, with stirring, a sufficient amount of ammonium sulfate to reach about 40% saturation (at 25° C.) with respect to ammonium sulfate. Ammonium sulfate is added over a period of two or more hours and at a temperature of 2° C. to 8° C.

The suspension is then stirred for a minimum of 10 hours at 2° C. to 8° C. and then centrifuged at approximately 4,500×g for 45 minutes or 14,000–22,000×g for 5 minutes at 2° C. to 8° C. The resulting solution is then diafiltered at 2° C. to 8° C. with about 7 volumes of sterile phosphate buffered saline in a hollow fiber cartridge having a molecular weight cut-off of about 5,000–10,000 daltons. Finally, the serum is filtered through a non-fiber releasing 0.22 micron Millipore filter. Prior to use, the serum is heated to 56° C. and held at that temperature for one hour to inactivate some complement components present in the serum.

When fractionation of the host's blood sample has been performed to remove erythrocytes and most granulocytes, the remaining cells which are to be subjected to polykaryon induction are suspended in a sufficient amount of the appropriate tissue culture medium to produce a final cell concentration of approximately $1-3\times 10^6$ cells per milliliter. For purposes of subsequent quantification, a cell differential can be performed on a small aliquot of suspended cells using, for example, a Giemsa stain. To protect the cells during preparation of the smear, human or animal serum is normally added to the cell suspension sample used to prepare the smear.

After the cell concentration has been adjusted, the cells are placed in an appropriate incubation vessel, such as, a 24-well tissue culture plate. For such a plate, approximately two milliliters of suspension are used per well so as to produce a cell density of approximately $10^6$ cells per square cm of bottom surface. The suspension is then incubated under suitable incubation conditions, for example, an incubation temperature of about 37° C. and an incubation atmosphere of humidified air containing 5% carbon dioxide.

To facilitate the quantification of polykaryon formation, a cover slip can be placed in the bottom of each well of the tissue culture plate prior to introduction of the suspension. After the incubation has been completed, the tissue culture plate is centrifuged causing the cells to be deposited on the cover slips. After removal of the supernatant, the cover slips with their attached cells can be removed from the wells and microscopically examined using standard techniques. This procedure provides for a more uniform collection of cells from patient to patient.

When fractionation of the host's blood sample has not been performed, the cells to be subjected to polykaryon induction are suspended in a sufficient amount of the appropriate tissue culture medium to produce a final concentration of between approximately 3.5 and $7\times 10^5$ cells per ml. Normally, a 1:10 to 1:20 dilution is required to obtain such a concentration, although other dilutions may be required as, for example, for patients having diseases such as leukopenia.

In performing the induction, it has been found important to use cells that have not been stored for an extended period of time. Specifically, it has been found preferable to use cells which have not been stored for longer than 24 hours at 4° C.

To induce polykaryon formation, a sufficient amount of Concanavalin A must be added to the incubation medium. Concentrations of Con A in the range of about 2.5 to about 40 micrograms per milliliter have been found sufficient to induce polykaryon formation, although concentrations as low as about 1.0 microgram per milliliter will also cause polykaryon formation. The preferred concentration range for Con A is between about 5 and about 10 micrograms per milliliter.

Purified, lyophilized Con A produced by various manufacturers can be used to induce polykaryon formation. For example, highly purified Con A produced by the Sigma Chemical Company (St. Louis, Mo.), the Vector Company (Burlingame, Calif.), Miles Laboratories (Elkhart, Ind.), Boehringer Mannheim (Indianapolis, Ind.) and P/L Biochemicals, Inc. (Milwaukee, Wis.) have been tested and found to produce the polykaryon response at the dosage levels described below.

Con A is typically added to the cell suspension at the beginning of the incubation. In about twenty hours, polykaryons which exhibit pronounced phagocytic activity are readily observed in the suspension, along with monocyte transformation into macrophages. The number and size of polykaryons will typically increase during the following two to three days. A typical sequence of events after the introduction of Con A to a leukocyte suspension obtained by the Ficoll-Hypaque technique is described in Table 1, infra. A similar series of changes occurs for the whole blood preparation.

The polykaryons and some of the macrophages, once formed, are found to be subject to invasion by activating T-lymphocytes (emperipolesis). The entering and intracellular lymphocytes display ultrastructural signs of cytotoxic T-cell clones: developed Golgi complexes, coated vesicles, and membrane-bound microvesicular, microtubular and dense bodies. The emperipolesis is followed by the destruction and eventual disappearance of the polykaryons during the week after exposure to Con A. Such a lectin-dependent cytotoxic emperipolesis directed towards nonmalignized self targets essentially differs from previously known cooperative lymphocytemonocyte responses to mitogens and antigens. It is believed that this form of emperipolesis may model an in vivo mechanism for elimination of monocyte-derived cells whose accessory or scavenger function in inflammatory granulomas has been completed.

The formation of polykaryons in response to stimulation by Con A can be followed by various manual and automated techniques. A convenient way to reveal polykaryons is by vital fluorescent microscopy techniques, using, for example, a stain such as acridine orange. A typical procedure for using this stain with a leukocyte culture is as follows. As described below, the same procedure can be used with the whole blood preparation, provided the erythrocytes are first removed so that the white blood cells can be seen.

Approximately one hour before examination, the culture is incubated with the acridine orange stain. Typically, one drop of a 0.1% acridine orange solution in 2 milliliters of culture is sufficient to produce the desired staining level. After the one hour period, the culture is collected into a 2 milliliter plastic Eppendorf tube and the cells are centrifuged in an Eppendorf centrifuge for three seconds at $15,000 \times g$. The supernatant is discarded and the pellet is resuspended in 0.1 ml of the culture medium, following which, it is placed on a slide and mounted under a cover slip.

Examination is most conveniently performed using a fluorescent microscope equipped with phase contrast optics and means for providing incident blue-violet exciting light. Such a microscope allows alternating fluorescent and phase contrast examination of a particular field of view. Typically, $10 \times$ and $40 \times$ objectives are used to examine the cell on the slide.

The slides are examined to obtain data regarding the following parameters: (1) the size of the polykaryons as indicated by the number of nuclei per polykaryon; and (2) the number of polykaryons produced based on the original monocyte population of the incubation sample. In terms of size, small polykaryons typically contain between 2 and 9 nuclei; medium sized polykaryons, between 10 and 20 nuclei; and large or giant polykaryons, more than 20 nuclei.

In terms of the number of polykaryons produced, a low production is typically on the order of 1 to 10 cells per approximately $10^5$ monocytes in the original population; a moderate production is between about 11 and about 50 cells; and a high production is more than about 50 polykaryons. As discussed above, a high yield of polykaryons and the simultaneous presence of small, medium and giant cells is indicative of a strong response to Con A and correlates with a normal level of cell-mediated immunity. On the other hand, a low yield and the lack of giant polykaryons indicates a low level of cell-mediated immunity.

For accurate quantification, it is important to collect as many cells as possible from the incubation vessel, including those cells attached to the walls of the vessel. Also, the complete area of the cover slip should be examined. As discussed above, a convenient way for ensuring complete and reproducible collection is to place a cover slip in the incubation chamber and centrifuge the cells directly once the cover slip.

Even more precise data can be obtained by using a cytocentrifuge, with a Giemsa stain, a periodic acid-Schiff (PAS) stain or a cytochemical stain for nonspecific esterase or acid phosphatase. A typical cytocentrifuge procedure is as follows.

First, the cell culture is thoroughly collected from the culture well into a 2 ml centrifuge tube and spun down by, for example, an Eppendorf centrifuge for three seconds at $15,000 \times g$. The supernatant is discarded and the pellet is resuspended in 0.1 ml of human or animal serum and placed into the sample chamber of a cytocentrifuge. A suitable cytocentrifuge is the "Cytospin-2" manufactured by the Shandon Company (Sewickley, Pennsylvania). Such a cytocentrifuge evenly distributes the cells in a sample over a limited round area of a slide, e.g., an area having a diameter of about 7 mm, and thus the complete smear can easily be examined by routine microscopy or by using an automatic microscope equipped with a scanning stage. Typically, for the cultures of the present invention, the smear should be prepared at $200 \times g$ for 10 minutes. This approach helps ensure complete sedimentation of all the cells onto the slide, including any giant polykaryons which may be present.

After the smears are obtained by the cytocentrifuge, they can be stained by a Giemsa or cytochemical stain. Normally, the stained smear should by dehydrated by alcohol, cleared by xylene and mounted in Permount so that microscopic examination can be made using 10×, 40× and oil immersion 100× objectives. As with the vital staining approach, it is necessary to examine the entire surface of the smear so as to identify all polykaryons produced.

The foregoing quantification schemes can also be applied to whole blood cultures which have not been fractionated to remove erythrocytes prior to incubation. In this case, the erythrocytes normally must be removed prior to staining and microscopic examination or their large number will make observation of the polykaryons difficult. A typical procedure for removing the erythrocytes is as follows.

The cell culture is collected into a 15 ml centrifuge tube having six volumes of 0.83% ammonium chloride. The cell culture-ammonium chloride solution is incubated at 37° C. for 15 minutes to lyse the red blood cells. The cells are then centrifuged at 3,000 rpm for 5 minutes and the supernatant including the hemoglobin and the red blood cell remnants is discarded. The cell pellet is resuspended in 0.1 ml serum and is placed into the sample chamber of the cytocentrifuge. The same cytocentrifugation, staining and microscope examination procedures as described above are then used to quantify the polykaryon production of the whole blood culture.

The following examples illustrate various aspects of the present invention. It is to be understood that these examples are provided for purposes of illustration only and are not to be construed as limiting the invention in any way.

cytocentrifuged and stained with a Giemsa or with a periodic acid-Schiff (PAS) stain, or were subjected to reaction for nonspecific esterase. The results are shown in FIGS. 1-5.

FIG. 1 shows a typical smear resulting from acridine orange staining. Giant (G) and small (S) polykaryons, surrounded by activated lymphocytes, are easily identified. FIGS. 2a and 2b show typical small and giant polykaryons at higher magnification. When viewed under blue-violet exciting light, the nuclei appear green and the lysosomes within the polykaryons appear red. The smaller cells surrounding the polykaryons are activated lymphocytes.

Figure 4:
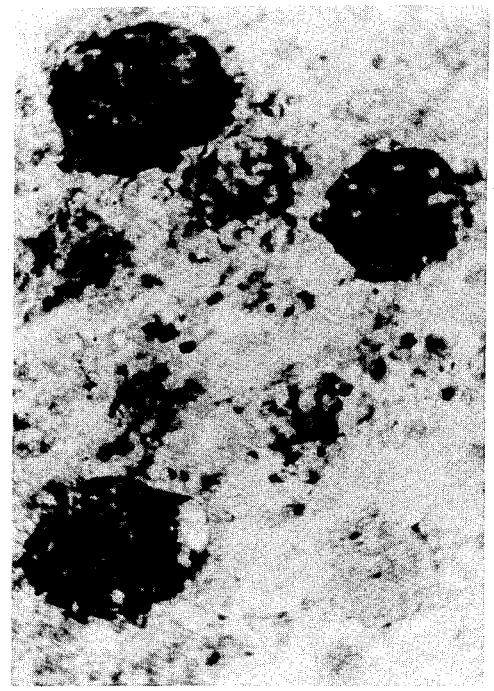
FIG. 4 is a photomicrograph at $20\times$ showing the results of staining a Con A-stimulated leukocyte culture from a normal individual with a periodic acid-Schiff (PAS) stain. Three polykaryons overloaded with PAS-positive material are seen.

FIGS. 3 and 4 illustrate the types of smears obtained with the cytocentrifuge-Giemsa stain (FIG. 3) and PAS stain (FIG. 4) procedures. For the PAS stain, the polykaryons appear to be rich in red granules when viewed in color because of their high polysaccharide content. As shown in these figures, these techniques easily and effectively identify polykaryons.

Figure 5:
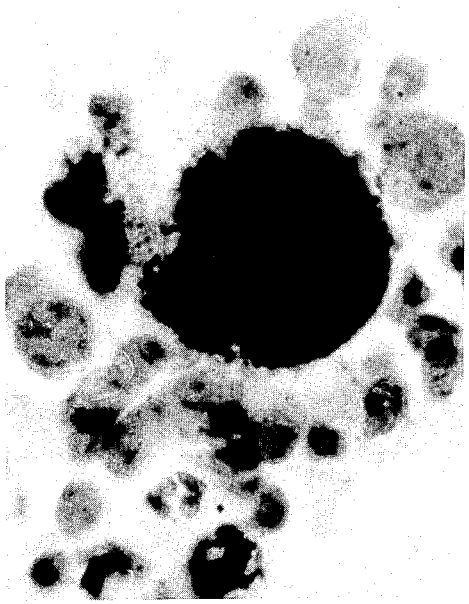
FIG. 5 is a photomicrograph at $100\times$ showing the results of a reaction for nonspecific esterase. A polykaryon overloaded by the reaction product is seen. The cell is surrounded by lymphocytes and granulocytes.

FIG. 5 shows, at a higher magnification (100×), the result of subjecting the polykaryons to a reaction for nonspecific esterase, which is a marker for cells of monocyte origin. As shown in this figure, the polykaryon is overloaded with granules produced by the reaction.

EXAMPLE 2

This example demonstrates the importance of using Concanavalin A as the mitogen for inducing polykaryon formation.

TABLE 1

CELLULAR RESPONSE TO CONCANAVALIN A OF LEUKOCYTE CULTURES
HOURS AFTER EXPOSURE OF THE CELL CULTURE TO CON A

| 24 | 48 | 72 |
|---|---|---|
| Cell Agglutination | Further Lymphocyte Activation; Mass Enlargement of the Cells, Accumulation of Lysosomes, Appearance of PHA-cells, Start of Proliferation | Strong Lymphocyte Activation and Mass Proliferation, Collections of Proliferation Cells Rich in Lysosomes, Numerous PHA-cells |
| Monocyte Aggregation | | |
| Lymphocyte-Monocyte Clumps | | |
| Start of Lymphocyte Activation: Enlargement of Nuclei and Nucleoli, Accumulation of Lysosomes | Clumps of Activated Lymphocytes Arranged around Activated Monocytes and Polykaryons | Numerous Polykaryons of Various Sizes, Some of Them with the Loss of Lysosomes, Vacuolation, and Lipid Degeneration |
| Appearance of Polykaryons (Mostly small and medium) | Strong Endocytic Activity of Monocytes | |
| Increase in Endocytic Activity of Monocytes | Increase in the Number and Size of the Polykaryons | |

Cultures contained $10^6$ cells per ml of medium and were exposed to 10 mg/ml of Con A

EXAMPLE 1

A series of leukocyte cultures were prepared from blood samples taken from healthy donors using the Ficoll-Hypaque, tissue culture and staining techniques described above.

In particular, the cultures were prepared within 24 hours of taking the samples from the donors. The cells were incubated in RPMI-1640 medium to which had been added 50 mg/ml of gentamicin and sufficient human aγ serum to produce a final serum concentration of between 5.0 and 20.0 percent. Con A was added to the medium at a concentration level of between 10 and 20 micrograms per milliliter. The cell concentration was adjusted to approximately $1 \times 10^6$ cells/ml and the cell suspensions were incubated in 24-well tissue culture plates for at least 20 hours at 37° C. and in humidified air containing 5% $CO_2$. Some cells were stained with an acridine orange stain, using the procedures described above, and observed under a fluorescent microscope equipped with phase contrast optics. Other cells were Leukocyte cultures were prepared using the same procedures as in Example 1, but were incubated with mitogens other than Con A. The mitogens teated were: phytohemagglutinins P and L, pokeweed mitogen, wolferia floribunda mitogen, antilymphocyte monoclonal antibody ORT-3 and staphylococcal enterotoxin A (SEA).

None of these motigens were capable of inducing the polykaryon response. In contrast, Concanavalin A consistently produces this response. Also, the response to Con A has been found to be independent of the commercial source of Con A in that purified Con A from Sigma, Vector, Miles, Boehringer Mannheim, and P/L Biochemicals will each produce the response.

EXAMPLE 3

This example demonstrates that the polykaryons are produced by the fusion of monocytes. It also shows that one or more lymphokines produced by activated T- lymphocytes may be involved in inducing the monocyte fusion.

A series of biochemical experiments were performed on polykaryons produced using the procedures of Example 1. It was found that the polykaryons displayed strong activity of nonspecific esterase. As known in the art, this enzyme is a cytochemical marker for monocytes and macrophages. In addition, the polykaryons were found to be rich in lysosomes and to show strong activity of acid phosphatase, again typical characteristics of cells of the monocyte-macrophage group.

Detailed examination of the polykaryons failed to reveal any nuclear divisions, indicating that polykaryon formation and growth are the result of fusion and subsequent recruitment of monocytes. Electron microscopy performed on polykaryons also showed that they result from the fusion of monocytes.

Observation of polykaryon cultures invariably showed that polykaryon formation is associated with lymphocyte activation. As described in Table 1, supra, appearance of polykaryons coincides with the start of lymphocyte activation (enlargement of nuclei and nucleoli, etc.). Subsequent growth of the polykaryons is accompanied by lymphocyte proliferation.

To test for the possible interactions between monocytes and lymphocytes in producing polykaryons, T-lymphocytes were removed form the culture by E-rosetting. The removal of T-lymphocytes was found to suppress both lymphocyte activation and polykaryon formation and growth despite the fact that the removal of the T-lymphocytes resulted in a decrease in the lymphocyte/monocyte ratio in the culture. Also, with the removal of T-lymphocytes, the emperipolesis phenomenon discussed above was also suppressed. The behavior of a T-lymphocyte depleted culture in comparison with a standard culture is described in Table 2.

Figure 6:
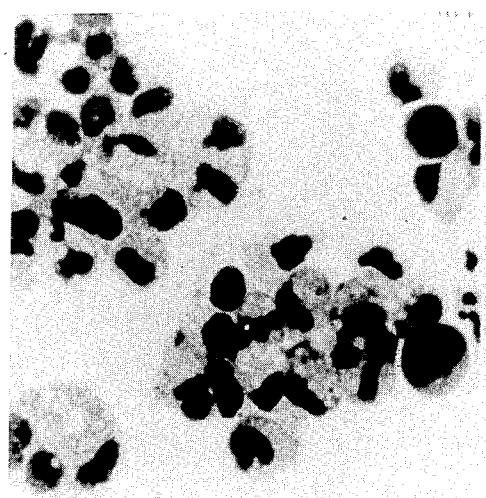
FIG. 6 is a photomicrograph (Giemsa stain) at $40\times$ showing the results of stimulating a leukocyte culture from a normal individual depleted of T-lymphocytes. Single activated lymphocytes and polykaryons containing 2 or 3 nuclei are seen.

FIG. 6 shows a Giemsa stain of a T-lymphocyte depleted culture. As shown in the figure, only small polykaryons containing 2 or 3 nuclei and single activated lymphocytes are seen.

Removal of Con A from the culture medium or washing of the cells with α-methyl mannoside after lymphocyte activation had been triggered was found to be ineffective in preventing polykaryon formation although their subsequent growth was somewhat suppressed.

Although not wishing to be bound by any particular theory of operation, the results of these studies on the interaction of lymphocytes with monocytes in polykaryon formation suggest that some lymphokines produced by activated T-lymphocytes are involved in the mechanism responsible for Con A dependent polykaryon formation.

It is to be understood that various modifications to the features of this invention can be made by those skilled in the art without departing from the invention's scope and spirit. Accordingly, it is not intended that the claims appended hereto be limited to the specific descriptions set forth herein, but rather that the scope of the claims be construed as encompassing all equivalents of the features of this invention.

TABLE 2

CELLULAR RESPONSE TO CONCANAVALIN A OF LEUKOCYTE CULTURES DEPLETED OF T-LYMPHOCYTES

| CULTURES | HOURS AFTER EXPOSURE OF THE CELL CULTURES TO CON A | | |
|---|---|---|---|
| | 24 | 48 | 72 |
| Standard Ficoll-Hypaque Leukocyte Culture <br> <u>G  L  M*</u> <br> 30  56  14 | Tight Agglutination <br><br> Start of Lymphocyte Activation | Tight Agglutination <br><br> Further Lymphocyte Activation, Start of Proliferation | Strong Lymphocyte Activation and Mass Proliferation <br> Numerous Polykaryons |
| Culture Depleted of T-Cells by E-Rosetting <br> <u>G  L  M*</u> <br> 15  24  61 | Single Polykaryons <br> Loose Agglutination <br> Normal Looking Lymphocytes | Numerous Polykaryons <br> Loose Agglutination <br> Enlargement of Some Lymphocytes <br><br> Increase in Endocytic Activity of Monocytes | Loose Agglutination <br> Single Activated and Mitotically Dividing Lymphocytes Scattered Among Normal Looking Cells <br> Appearance of Small (2–5 Nuclei) Polykaryons |

*Cell differential in the culture: percent of granulocytes (G), lymphocytes (L), and monocytes (M).

What is claimed is:

1. A method for determining levels of cell-mediated immunity by assaying autologous cells, comprising the steps of:
   obtaining a whole blood sample from a host;
   incubating cells comprising monocytes from the sample in a tissue culture medium containing Concanavalin A for between 18 and 48 hours; and
   observing the number of short-lived monocyte polykaryons produced or the increase in number of nuclei per polykaryon or both to thereby determine the level of cell-mediated immunity of the host from which the blood sample was obtained.

2. The method of claim 1 wherein erythrocytes in the blood sample are removed from the sample prior to incubating the cells in the tissue culture medium.

3. The method of claim 2 wherein the tissue culture medium includes protein.

4. The method of claim 3 wherein the protein concentration is between about 1.00 mg/ml and about 6.00 mg/ml.

5. The method of claim 1 wherein the cell concentration in the tissue culture medium is between approximately $10^4$ and approximately $10^8$ cells per milliliter.

6. The method of claim 5 wherein the cell concentration in the tissue culture medium is between approximately $1 \times 10^6$ and $3 \times 10^6$ cells per milliliter.

7. The method of claim 1 wherein the cells are not stored for an extended period of time prior to being incubated in the tissue culture medium.

8. The method of claim 7 wherein the cells are not stored for a period longer than 24 hours at 4° C. before being incubated in the tissue culture medium.

9. The method of claim 1 wherein the concentration of Concanavalin A is between approximately 2.5 and approximately 40 micrograms per milliliter of tissue culture medium.

10. The method of claim 9 wherein the concentration of Concanavalin A is between approximately 5 and approximately 10 micrograms per milliliter of tissue culture medium.

11. The method of claim 1 wherein the polykaryons are observed after being vitally stained with an acridine orange stain.

12. The method of claim 1 wherein the polykaryons are observed after being stained with a stain selected from the group consisting of a periodic acid-Schiff stain for polysaccharides, a stain for nonspecific esterase, and a stain for acid phosphatase.

* * * * *